(12) United States Patent
de Vries et al.

(10) Patent No.: US 11,558,953 B2
(45) Date of Patent: Jan. 17, 2023

(54) EMC CONTROL FOR PULSED HIGH VOLTAGE SOURCE OF A PLASMA DEVICE FOR MEDICAL TREATMENT

(71) Applicant: PlasmaCure B.V., Nijmegen (NL)

(72) Inventors: Douwe Henrik de Vries, Eindhoven (NL); Paulien Smits, Eindhoven (NL); Wouter Bastiaan Zeper, Eindhoven (NL)

(73) Assignee: PLASMACURE B.V., Nijmegen (NL)

( * ) Notice: Subject to any disclaimer, the term of this patent is extended or adjusted under 35 U.S.C. 154(b) by 309 days.

(21) Appl. No.: 16/954,915

(22) PCT Filed: Dec. 18, 2018

(86) PCT No.: PCT/NL2018/050852
§ 371 (c)(1),
(2) Date: Jun. 17, 2020

(87) PCT Pub. No.: WO2019/125149
PCT Pub. Date: Jun. 27, 2019

(65) Prior Publication Data
US 2020/0396820 A1    Dec. 17, 2020

(30) Foreign Application Priority Data
Dec. 19, 2017   (NL) ...................................... 2020126

(51) Int. Cl.
*H05H 1/24* (2006.01)
*A61N 1/04* (2006.01)
*A61N 1/44* (2006.01)

(52) U.S. Cl.
CPC ......... *H05H 1/2406* (2013.01); *A61N 1/0472* (2013.01); *A61N 1/44* (2013.01)

(58) Field of Classification Search
CPC ...... H05H 1/2406; A61N 1/0472; A61N 1/44; A61N 1/0476; A61N 1/0492; A61N 1/40; A61N 1/0408
See application file for complete search history.

(56) References Cited

U.S. PATENT DOCUMENTS

| 2004/0097914 A1 | 5/2004 | Pantera et al. |
| 2013/0068226 A1 | 3/2013 | Watson et al. |

FOREIGN PATENT DOCUMENTS

WO   WO 2016/186501 A2   11/2016

OTHER PUBLICATIONS

European Patent Office, International Search Report in corresponding International Application No. PCT/NL2018/050852, dated Mar. 28, 2019 (2 pages).

*Primary Examiner* — Mark W. Bockelman
(74) *Attorney, Agent, or Firm* — Leydig, Voit & Mayer, Ltd.

(57) ABSTRACT

The invention relates to a high voltage source to be coupled to an electrode arrangement for a dielectric barrier discharge plasma treatment. It has a high voltage transformer device including a primary and secondary inductor coupled via a magnetic circuit. A feed circuit including a power capacitor, the power capacitor coupled with the primary inductor and a first controllable conductor in series. A controller is arranged to intermittent switching of the first controllable conductor in on- and off-states; and a second controllable conductor is coupled in parallel to the primary windings; the controller arranged to switch the second controllable conductor to a conducting on-state when the first controllable conductor is in an on-state to short the resonating current in the primary inductor.

16 Claims, 8 Drawing Sheets

EMC CONTROL FOR PULSED HIGH VOLTAGE SOURCE OF A PLASMA DEVICE FOR MEDICAL TREATMENT

CROSS-REFERENCE TO RELATED APPLICATIONS

This patent application is a U.S. National Phase of PCT International Application No. PCT/NL2018/050852, filed Dec. 18, 2018, which claims priority to The Netherlands Application No. 2020126 filed Dec. 19, 2017, which are both expressly incorporated by reference in their entireties, including any references contained therein.

FIELD OF THE INVENTION

This invention relates to devices for generating non-thermal plasma. In particular, the invention relates to devices that can be applied for treatment living tissue.

BACKGROUND OF THE INVENTION

Cold plasmas have considerable potential for, amongst others, skin conditioning, disinfection of skin and wound healing. However, available plasma sources lack the possibility to treat larger areas, to control plasma properties and/or the possibility to adapt the shape of the plasma to the shape of the object to be treated (e.g. a foot).
  Cold plasmas allow efficient and painless treatment of living tissue, even in microscopic openings, without damaging healthy tissue.
  The bacterial response to plasma application is almost instantaneous (few seconds).
  From U.S. Pat. No. 9,005,188 and EP2670477 flexible mesh electrodes are known with a structured surface of a plurality of spaced apart projections from the surface to form air-guiding areas where the plasma is generated. A problem associated with these devices is the high voltage (HV) oscillations, that is caused by irregular discharges of the plasma. This poses problems for electromagnetic compatibility. It is found that the plasma pad itself is the biggest source of radiation because high voltage is applied to an open mesh that will act as a radio antenna emitting electromagnetic radiation. The pulsed operation of the plasma will be briefly explained here with reference to the cold plasma device shown in FIG. 1. The plasma may be powered by repetitive, short high-voltage pulses (ns-µs duration, up to a few 100 kHz repetition rate). A high voltage source 600 is provided for driving the planar electrode. The high voltage source 600 drives the planar electrode in a pulsed voltage in a range of 3-8 kV, in a range of 0.5-100 kHz, and a pulse duration in a range of 1 nano to 150 micro second. This allows for a pulse rate that substantially provides a micro discharge wherein electrical current through the object to be treated (skin, human body) will only flow during the time that the plasma is on (which is typically equal to the HV pulse duration). In between the pulses, the plasma is not active, and no current flows through the skin.
  The pulsed operation of the plasma enables control over the power of the plasma by means of the pulse repetition rate. In this way, the plasma power can be controlled and adjusted without affecting the plasma properties. For a device that is to be used in home and medical care environments the power circuit for generating a high voltage, in combination with the plasma on an open pad electrode, can produce a lot of interference. One of the known power circuits is an oscillating high voltage circuit. FIG. 3 shows an example of such a pulsed high voltage circuit which is highly oscillating circuit as the leakage inductance of the transformer T1 resonates with capacitor C1. It is an aim to improve the circuit characteristics, in order to reduce the generation of unwanted oscillations that produce electromagnetic interference, in particular in a range of 50 MHz. However, a pulsed high voltage circuit of the type as disclosed therein is not capable of providing pulsed power, necessary for igniting a plasma suitable for treatment of tissue.

SUMMARY OF THE INVENTION

In summary, embodiments of the invention pertain to: a high voltage source to be coupled to an electrode arrangement for a dielectric barrier discharge plasma treatment of an irregularly three-dimensionally shaped surface of an electrically conducting body, which surface is used as a counter electrode, having
  a high voltage transformer device including a primary and secondary inductor coupled via a magnetic circuit; the secondary inductor to be coupled to the electrode arrangement;
  a power capacitor coupled to a feed circuit for feeding the power capacitor, the power capacitor coupled with the primary inductor and a first controllable conductor in series; to provide a pulsed primary current in the primary inductor resonating with the capacitor when the first controllable conductor is switched in a conducting on-state; and to feed the capacitor with electrical current when the first controllable conductor is switched in a non conducting off-state;
  a controller; the controller arranged to intermittent switching of the first controllable conductor in on- and off-states; and a second controllable conductor coupled in parallel to the primary windings; the controller arranged to switching the second controllable conductor to a conducting on-state when the first controllable conductor is in an on-state to short the resonating current in the primary inductor.
  It is found that the EM oscillations originate from resonant antenna behavior of the plasma pad, in combination with the HV cable. It is thought that by shorting the primary inductor, electromagnetic power of the high voltage transformer is drained which stops oscillating currents in the plasma pad.

DETAILED DESCRIPTION

Figure 1A:
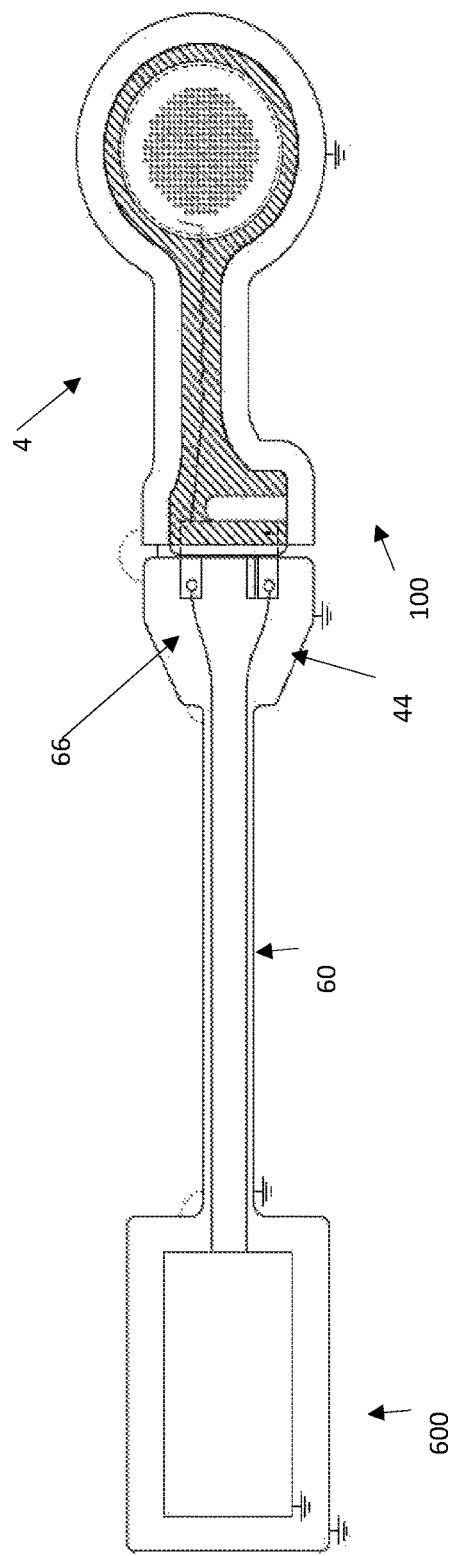
FIG. 1A shows a schematic perspective view of a system configuration of the cold plasma device.

FIG. 1A shows a schematic perspective view of a cold plasma device including a high voltage source to be coupled to the electrode arrangement 100. The plasma device 100 provides a dielectric barrier discharge (DBD) technique for plasma generation.

Due to the pulsed operation, treatments can be performed at adjustable and controllable pulse sequences, duty cycles and bursts of pulses with varying duration. Pulse sequences can be optimized towards a specific application. To achieve a good electromagnetic compatibly for the complete system 600 a protective earth shielding 44 is provided to screen off the cable 60, reducing the radiation from the cable. The shielding 44 may be attached to the grounded casing of the source 600. The same grounded shielding 44 of the casing can be connected, via a connector 66 to the shielding 4 of the plasma device 100 and thereby completely screen of the treatment area. Some ferrite cores on the output of the source may filter the frequencies induced by the HV transformer on the cable, and reduces the radiation of the common mode. Also the shielding of the HV Transformer should be such that it reduces the outgoing radiation and reduce the internal interference on the power electronics.

Figure 1B:
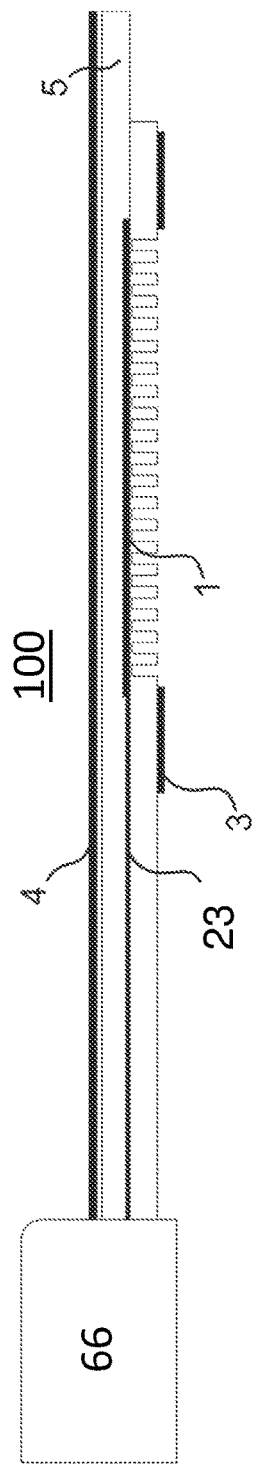
FIG. 1B shows the device of FIG. 1 in schematic cross sectional view.

FIG. 1B shows that the plasma device 100 formed by a planar substrate 5 containing a planar electrode 1, that is covered with a dielectric foil or film. A gas (or air) gap is present in a treatment area formed between an object to be treated (e.g. foot) functioning as a counter electrode and dielectric with a dielectric constant e.g. larger than 2. The treatment area may be bounded by reference electrode 3. Electrode 1 can be made from metal foil, but a mesh is suitably adaptable to the 3D shape, and will not rupture, crease or fold. The electrode 1 may be contacted by a lead 23, that connects to a high voltage clamp, and a reference electrode clamp that connects to the reference electrode 3 respectively. Reference electrode 3 may be provided in an edge portion. Electrode 3 is in contact with the skin to be treated. If the electric field is high enough (>30 kV/cm) and if the thickness of the air gap is rather constant, homogeneously distributed cold plasma discharges are created in the air gap to the object to be treated (e.g. the skin of a foot). Dielectric and protrusions have a high dielectric strength, e.g. >180 kV/mm.

Accordingly an electrode arrangement 100 is shown for a dielectric barrier discharge plasma treatment of an irregularly three-dimensionally shaped surface of an electrically conducting body. The body is typically a human body part, such as a foot, heel, toe, finger or any other diseased skin part, which surface is used as a counter electrode.

Figure 2:
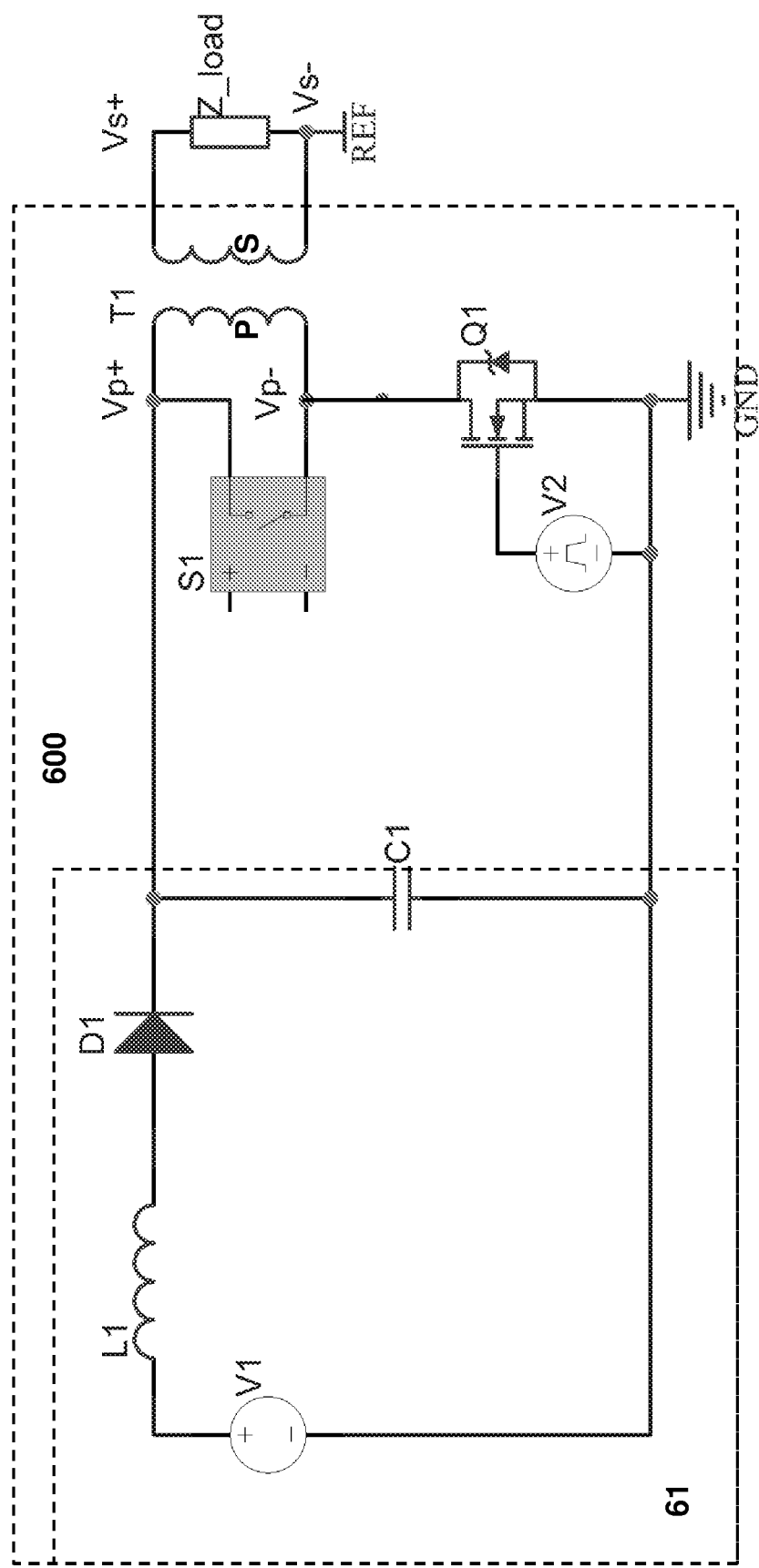
FIG. 2 shows a pulsed high voltage power source without termination.

FIG. 2 in more details shows a high voltage source 600 to be coupled to an electrode arrangement (Z_Load) for a dielectric barrier discharge plasma treatment. The source 600 comprises a high voltage transformer device T1 including a primary P and secondary S inductor coupled via a magnetic circuit; the secondary inductor S to be coupled to the electrode arrangement—here schematically indicated as Z_load. A feed circuit 61 includes a power source, an inductor L1 and a unidirectional current conductor D1 coupled in series to a power capacitor C1. The power source feeds electrical current into the capacitor device power capacitor C1, which is coupled with the primary inductor P and a first controllable conductor Q1 in series; to provide a pulsed primary current in the primary inductor P resonating with the capacitor C1 when the first controllable conductor is switched in a conducting on-state.

Figure 3:
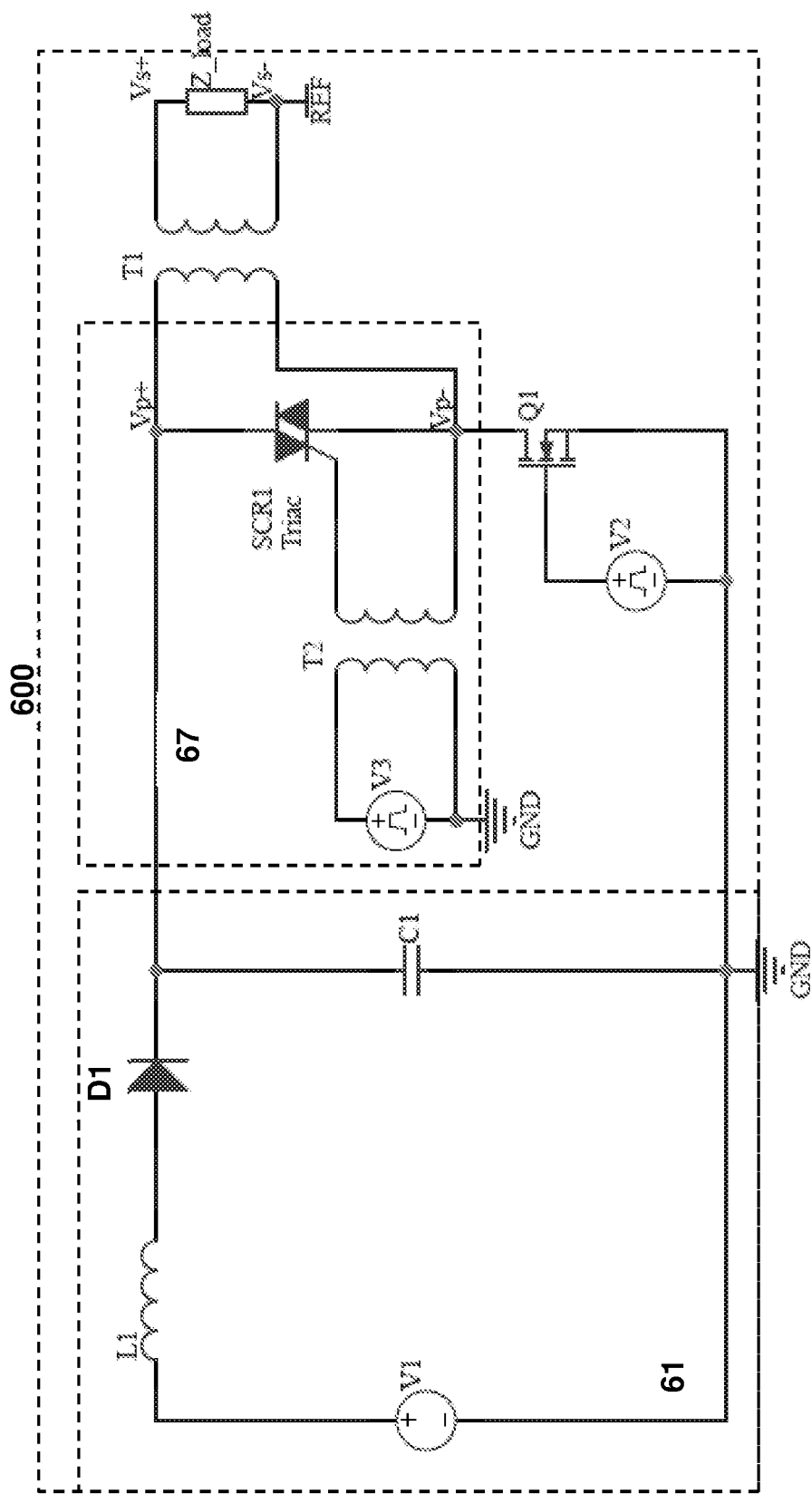
FIG. 3 shows a pulsed high voltage power source with a triac circuit.

If Q1 is off, that is, the switch is open in a non conducting off-state, the voltage over capacitor C1 can be boosted with electrical current. A second controllable conductor switch S1 is coupled in parallel to the primary windings P. A controller is programmed to control timing of the switches Q1 and S1. When the first switch Q1 is in an on-state, S1 is switched off after a pulse few cycles (e.g. 3-10) to short the resonating current in the primary inductor. The later pulses will not contribute to plasma forming anymore, so that shorting the primary will stop driving the EM oscillations in the load. In principle, the switching of S1 can be carried out by a suitable switch, but it appears that the primary voltage spikes Vp+-Vp− may be several hundreds of Volts (amplified by transformer T1 to several thousands of Volts). Preferably, the second controllable conductor comprises a control terminal that is galvanically disconnected from the primary inductor P. FIG. 3 shows a further enhancement of the circuit disclosed in FIG. 2, having a circuit section 67 arranged to short the resonating current in the primary inductor, switched by a control terminal V3. Triac is triggered by a secondary winding of pulse transformer T2, that is powered by voltage controller V3 on the primary winding and is galvanically isolated from the transformer T1. Triac SCR1 (silicon controlled rectifier) is a bi-directional thyristor that has a gate trigger, which brings the triac into conduction mode when triggered. By this design, the triac, as a 'second conductor' arranged to short the resonating current in the primary inductor is switched by a control terminal that is galvanically disconnected from the primary inductor. The pulse transformer is electrically designed to deliver a pulse in the secondary winding, if the primary winding receives a pulsed voltage input. This can be achieved by a pulse transformer with a suitable ET constant (e.g. 300-500 voltmicroseconds) for a pulse duration of about 100-150 microseconds.

Figure 4:
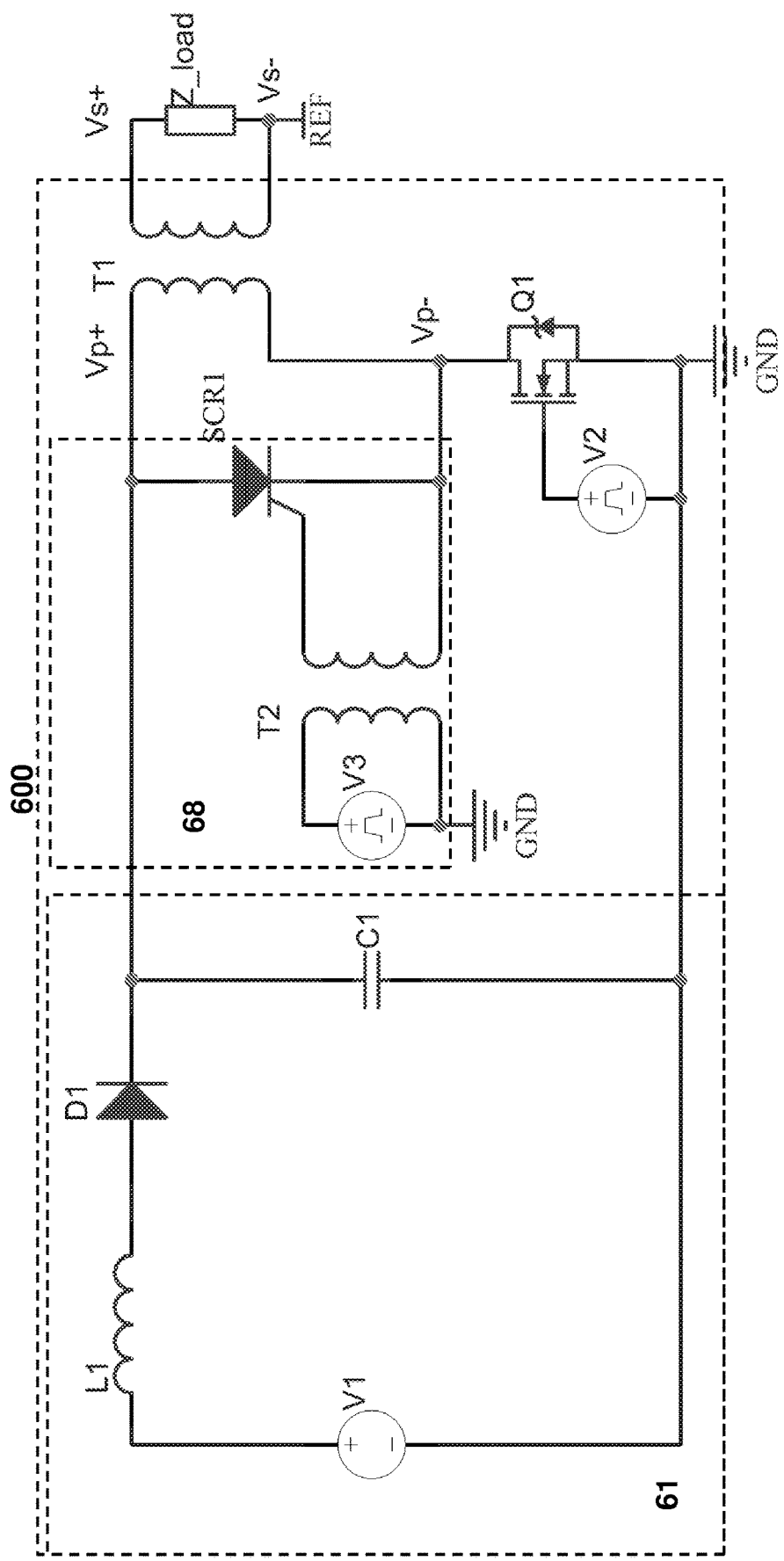
FIG. 4 shows a pulsed high voltage power source with a thyristor circuit.
Figure 5:
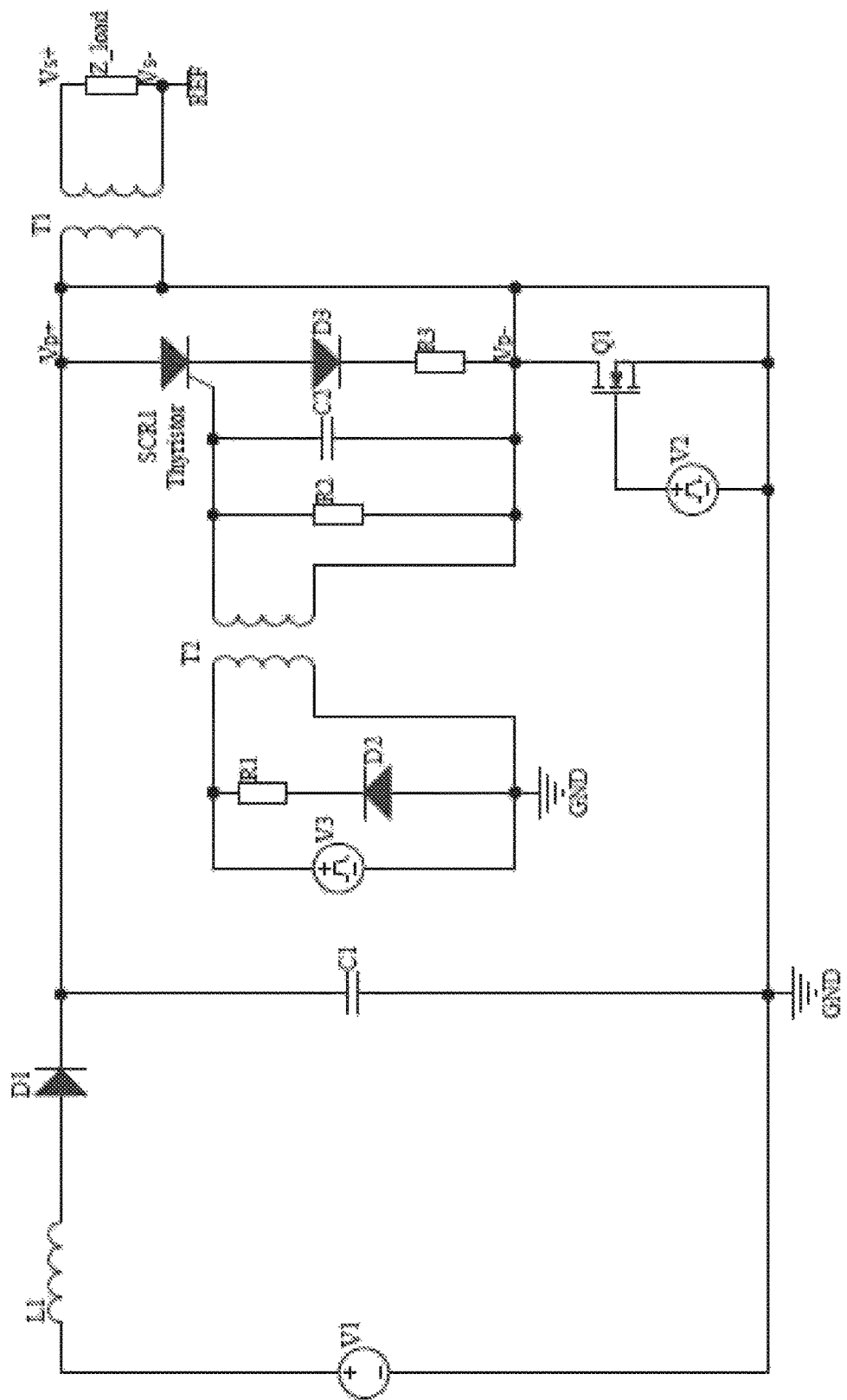
FIG. 5 shows a pulsed high voltage power source with thyristor and suppression circuits.

A particularly suitable solution for this second switch circuit 68 is found in FIG. 4, where the second controllable conductor comprises a silicon controlled rectifier (SCR) having a gate that is magnetically coupled via an transformer to a controller circuit. In this design, the SCR is implemented by a thyristor. A thyristor device has the advantage of a unidirectional current control. While a thyristor seems to have disadvantages over the triac, since it limits the controllable conduction mode in a single direction only, therefore only shorting half of the oscillations over the inductor, it appears to be more reliable in gate control to prevent misfires when the primary inductor is oscillating. As an alternative to a galvanically isolated gate, an optocoupler device can be used that switches a diode by electromagnetic radiation. Once conducting, it is on, until the current drops below a threshold value. The gate of the thyristor is in this design coupled to the primary inductor, which is a challenge for the control of the device due to the oscillating characteristics of the voltage over the inductor. As an example, the trigger pulse is sent 10 microseconds later than the Q1, Q2 switched conductors. In a further example the SCR1 is switched to a conducting on-state within a timeframe ranging from 5-50 microseconds when the first controllable conductors Q1, Q2 are switched into an on-state. In FIG. 5, an alternative embodiment is illustrated. In this embodiment, a primary snubber is provided on primary side of pulse transformer T2, for protecting the voltage controller V3. When a voltage drops over the primary side due a controlled current flow path is provided via resistor R1 and diode D2. On the secondary side, a high frequency filter formed by R2 and capacitor C2 is provided that prevents that the Thyristor gate SCR1 will pick up high frequency voltages EMI provided by the pulse transformer. In addition to that, as a further enhancement, a power diode and resistor is included in the circuit of the thyristor, to prevent inadvertent rising of the anode voltage, which could trigger misfires. Thyristor SCR1 has in an exemplary embodiment a blocking voltage of 800 V and is capable of conducting 250 A peak current. The on-state voltage is 1.8 V and a trigger current is about 9 mA. Depending on whether Thyristor anode is coupled to Vp+ or Vp− any of the oscillation flanks of the circuit can be selected.

Figure 6:
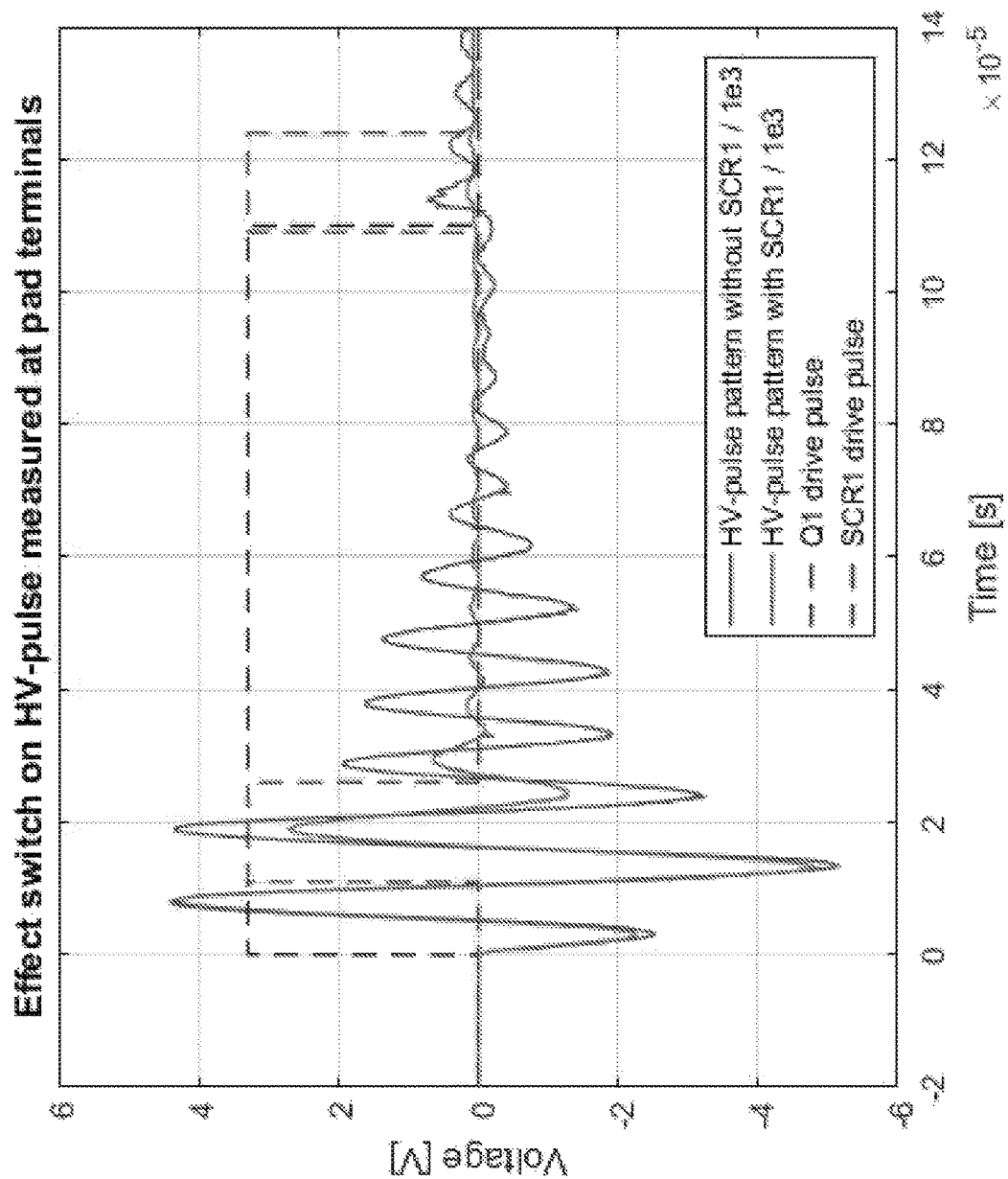
FIG. 6 shows the effect of the switch on the HV output.

FIG. 6 shows a reduced number of oscillations for a HV-pulse with a controllable switch to short the resonating current in the primary inductor. The effect of the controllable switch SCR is shown on the output voltage Vs+. Q1 starts conducting at t=0 μs. At t=11 μs the SCR1 driving signal becomes high. It is clear that after t=11 μs the oscillations dampen more quickly when utilizing the SCR1 switch. The pulse width of the SCR1 drive pulse has a maximum as the pulse transformer cannot sustain long pulses. For FIG. 6, the SCR drive pulse length is 15 μs. So, at t=26 μs the SCR1 drive signal becomes low. At t=104 μs, slightly before the end of the Q1 drive pulse, the SCR1 drive pulse becomes high again. This is done such that the oscillations caused by the turn-off of Q1 are dampened out. At t=105 μs the Q1 drive signal becomes low and at t=119 μs the SCR1 drive signal becomes low. This sequence can be repeated at a variable frequency. The so-called firing delay of SCR1 can also be adjusted in order to allow more or less oscillations.

Clearly the load voltage measured dies out after three oscillations of about 50-80 microseconds; in contrast to more than 8 after that period; where the EM bursts concentrate and are lower in the first three oscillations, and substantially lower after the first three oscillations.

Figure 7:
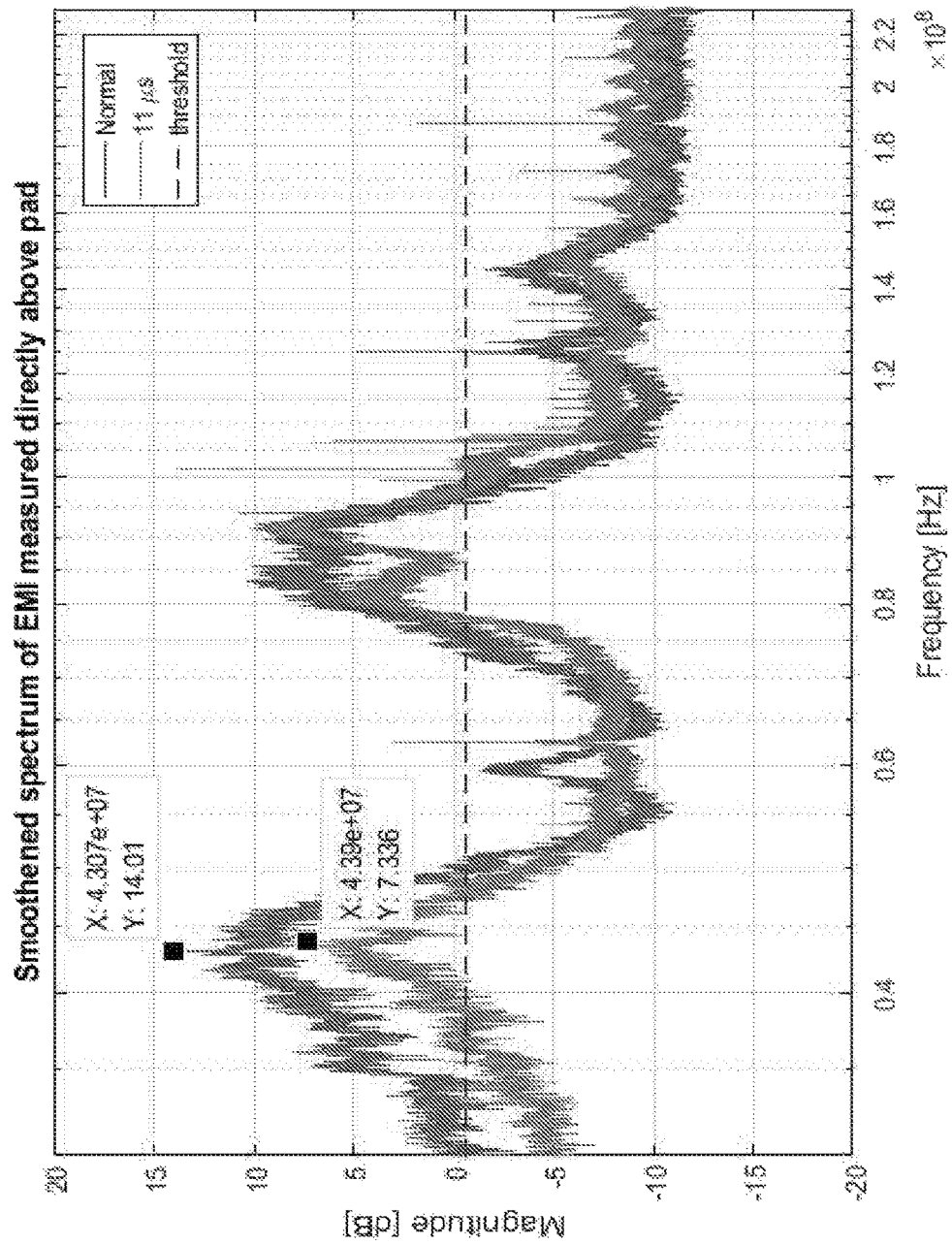
FIG. 7 shows the effect of the switch on the EMI spectrum.

Similarly, FIG. 7 shows the spectrum of EMI frequencies, substantially reduced by about 5 dB for subgigaHertz frequencies.

Figure 8:
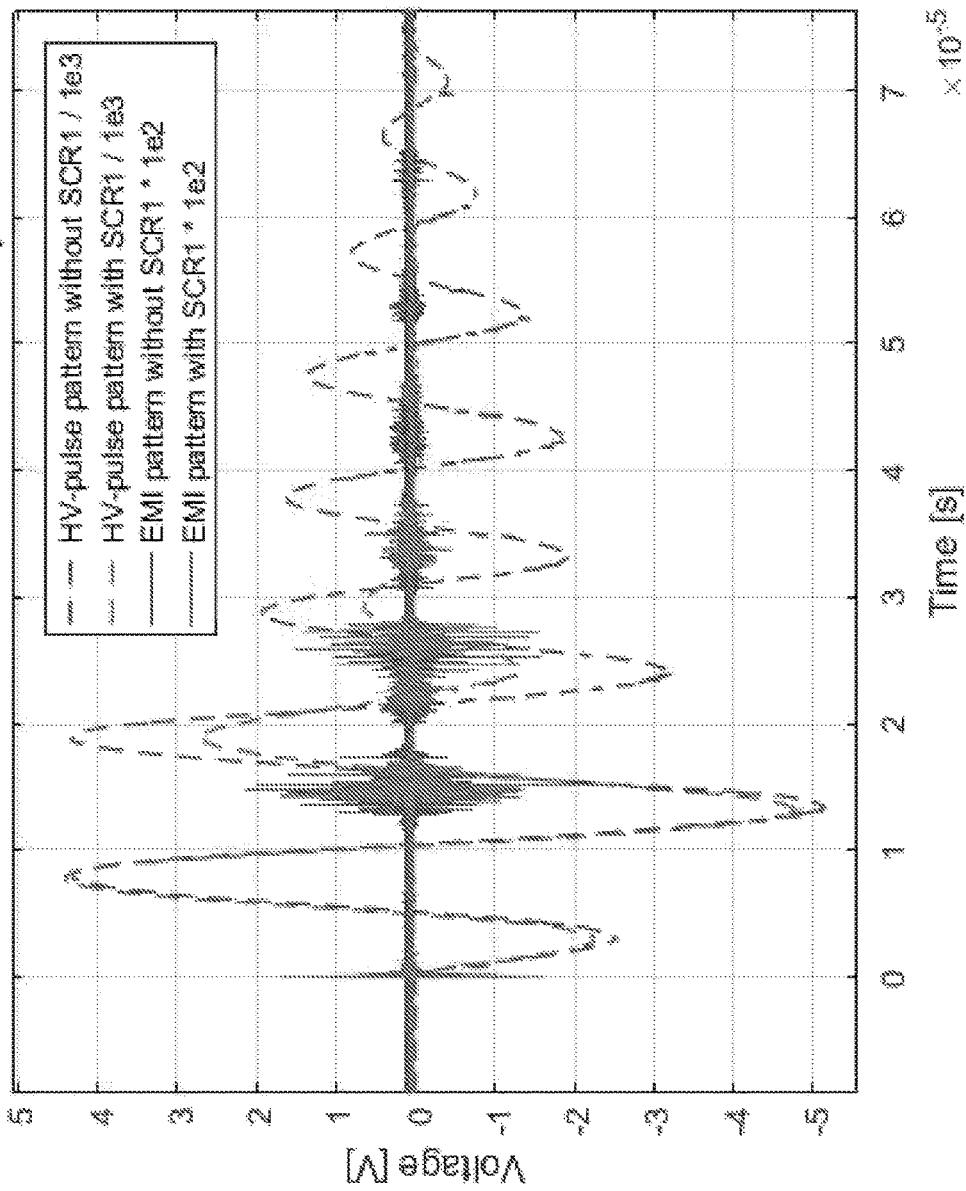
FIG. 8 shows the effect of the switch on the EM radiated by the pad.

FIG. 8 depicts the effect on the EM radiated by the pad. It can be seen that there are EM bursts, which seem to correlate with the zero-crossings of the HV-pulse. By utilizing the switch, the amount of EM bursts is reduced, thus providing less electromagnetic interference.

FURTHER EMBODIMENTS

The flexible plasma device is a platform technology with a number of interesting applications and market possibilities for medical treatments and prevention measures. In dermatology, new opportunities are being opened for wound healing, tissue regeneration, therapy of skin infections, and probably many more applications. Also, plasmas may effectively kill skin-cancer cells. A few examples:

Skin diseases: Most dermatological problems are associated with bacterial or fungal infections. Plasmas may help to reduce complications due to bacteria and fungi, and may even treat the diseases themselves.

Chronic wounds and inflammations: Plasmas may very well assist in controlling the consequences of chronic inflammation associated with these diseases by eliminating bacterial and fungal infections, which results in a drastic improvement of the quality of life. Additionally, plasma may improve wound healing by stimulating human cells and microcirculation of the blood.

Hospital hygiene: The growth of resistant bacteria (e.g. MRSA) poses a big problem in hospitals. Plasma devices can sterilize or disinfect both medical tools and hands (e.g. of surgeons).

Antifungal treatment: It has been shown that plasmas can be employed efficiently to combat fungal diseases.

The plasma can easily be delivered to the skin, e.g. in the form of a plasma pad. The plasma is directly in contact with the skin, which may enhance its effects via reactive oxygen and nitrogen species and considerable, transient electric fields (several kV/cm). The skin will be temporarily exposed to the plasma to disinfect the skin and to stimulate skin cells (e.g. to proliferate and migrate) and microcirculation of the blood. Typically, one-minute plasma treatment will reduce the bacterial load on the skin significantly, while stimulating human cells and microcirculation. Such a treatment should be continued until the desired clinical effect has been obtained.

The invention claimed is:

1. A high voltage source to be coupled to an electrode arrangement for dielectric barrier discharge plasma treatment of living tissue, the high voltage source comprising:
a high voltage transformer device including a primary inductor and a secondary inductor that are coupled via a magnetic circuit; wherein the secondary inductor is to be coupled to the electrode arrangement;
a feed circuit including a power capacitor, wherein the power capacitor is coupled with the primary inductor and a first controllable conductor in series to:
provide a pulsed primary current in the primary inductor resonating with the capacitor when the first controllable conductor is switched in a conducting on-state; and
feed the power capacitor with electrical current when the first controllable conductor is switched in a non-conducting off-state;
a controller arranged to cause an intermittent switching of the first controllable conductor between the on-state and the off-state; and
a second controllable conductor coupled in parallel to the primary inductor;
wherein the controller is arranged to switch the second controllable conductor to a conducting on-state, when the first controllable conductor is in an on-state, to short circuit a resonating current in the primary inductor, and
wherein the second controllable conductor comprises a silicon controlled rectifier having a gate that is coupled via an inductor to a controller circuit, the controller circuit being magnetically coupled to the inductor.

2. The high voltage source of claim 1, wherein the second controllable conductor comprises a control terminal that is galvanically disconnected from the primary inductor.

3. The high voltage source of claim 1, wherein the controller is arranged to cause a switching of the second controllable conductor to a conducting on-state, wherein the switch occurs within a timeframe ranging from 5-50 microseconds when the first controllable conductor is switched into an on-state.

4. The high voltage source of claim 1, wherein the feed circuit includes a power source, an inductor and a unidirectional current conductor coupled in series to the power capacitor, for feeding electrical current into the power capacitor.

5. The high voltage source of claim 1, wherein the first controllable conductor is bidirectional.

6. The high voltage source of claim 1, wherein the second controllable conductor is unidirectional.

7. The high voltage source according to claim 1, wherein the controller drives the high voltage transformer to a pulsed voltage in a range of 3-8 kV, repetition rate in a range of 0.5-100 kHz, and a pulse duration in a range of 1 nano-150 micro second.

8. An arrangement including a high voltage source, coupled to an electrode arrangement,
wherein the high voltage source comprises:
a high voltage transformer device including a primary inductor and a secondary inductor that are coupled via a magnetic circuit; wherein the secondary inductor is to be coupled to the electrode arrangement;
a feed circuit including a power capacitor, wherein the power capacitor is coupled with the primary inductor and a first controllable conductor in series to:
provide a pulsed primary current in the primary inductor resonating with the capacitor when the first controllable conductor is switched in a conducting on-state; and
feed the power capacitor with electrical current when the first controllable conductor is switched in a non-conducting off-state;
a controller arranged to cause an intermittent switching of the first controllable conductor between the on-state and the off-state; and
a second controllable conductor coupled in parallel to the primary inductor;
wherein the controller is arranged to switch the second controllable conductor to a conducting on-state, when the first controllable conductor is in an on-state, to short circuit a resonating current in the primary inductor, and
wherein the second controllable conductor comprises a silicon controlled rectifier having a gate that is coupled via an inductor to a controller circuit, the controller circuit being magnetically coupled to the inductor; and
wherein said electrode arrangement comprises:
a first electrode to be coupled to the high voltage source via a first lead;
a dielectric is formed by a flexible material in such a way that the dielectric shields the first planar electrode from the surface to be treated; and
a spacer defining a structured surface on a side of said arrangement facing a surface to be treated,
wherein the first electrode is fitted to an object to be treated and brought in contact with the dielectric.

9. The arrangement including a high voltage source, coupled to an electrode arrangement of claim 8, wherein the first lead connects to a high voltage clamp, and wherein the second lead connects to a reference voltage clamp.

10. The arrangement including a high voltage source, coupled to an electrode arrangement of claim 8, wherein the first electrode is a stretchable mesh.

11. The arrangement including a high voltage source, coupled to an electrode arrangement of claim 8, wherein the second controllable conductor comprises a control terminal that is galvanically disconnected from the primary inductor.

12. The arrangement including a high voltage source, coupled to an electrode arrangement of claim 8, wherein the controller is arranged to cause a switching of the second controllable conductor to a conducting on-state, wherein the switch occurs within a timeframe ranging from 5-50 microseconds when the first controllable conductor is switched into an on-state.

13. The arrangement including a high voltage source, coupled to an electrode arrangement of claim 8, wherein the feed circuit includes a power source, an inductor and a unidirectional current conductor coupled in series to the power capacitor, for feeding electrical current into the power capacitor.

14. The arrangement including a high voltage source, coupled to an electrode arrangement of claim 8, wherein the first controllable conductor is bidirectional.

15. The arrangement including a high voltage source, coupled to an electrode arrangement of claim 8, wherein the second controllable conductor is unidirectional.

16. The arrangement including a high voltage source, coupled to an electrode arrangement of claim 8, wherein the controller drives the high voltage transformer to a pulsed voltage in a range of 3-8 kV, repetition rate in a range of 0.5-100 kHz, and a pulse duration in a range of 1 nano-150 micro second.

* * * * *